(12) United States Patent
Matsunaga et al.

(10) Patent No.: US 7,923,142 B2
(45) Date of Patent: Apr. 12, 2011

(54) ONIUM SALT, ELECTROLYTE FOR NONAQUEOUS CELL CONTAINING THE NOVEL ONIUM SALT FOR NONAQUEOUS CELL AND METHOD FOR OPTIMIZING NEGATIVE ELECTRODE USING ELECTROLYTE CONTAINING ONIUM SALT

(75) Inventors: Tomonori Matsunaga, Tsukuba (JP);
Takeo Kawahara, Funabashi (JP);
Hajime Matsumoto, Ikeda (JP)

(73) Assignees: Tokuyama Corporation (JP); National Institute of Advanced Industrial Science and Technology (JP)

( * ) Notice: Subject to any disclaimer, the term of this patent is extended or adjusted under 35 U.S.C. 154(b) by 215 days.

(21) Appl. No.: 11/870,058

(22) Filed: Oct. 10, 2007

(65) Prior Publication Data
US 2008/0039634 A1    Feb. 14, 2008

Related U.S. Application Data

(62) Division of application No. 10/485,448, filed as application No. PCT/JP02/07666 on Jul. 29, 2002.

(30) Foreign Application Priority Data

Jul. 31, 2001  (JP) ................................ 2001-231262
Oct. 31, 2001  (JP) ................................ 2001-335029
Nov. 19, 2001  (JP) ................................ 2001-352963

(51) Int. Cl.
*H01M 2/16* (2006.01)
*H01M 10/40* (2006.01)
*C07D 233/00* (2006.01)

(52) U.S. Cl. ..................... 429/137; 429/186; 548/300.4; 548/123

(58) Field of Classification Search .................. None
See application file for complete search history.

(56) References Cited

U.S. PATENT DOCUMENTS

| 3,833,597 | A  | * | 9/1974  | Hardy et al. ............... 546/336 |
| 6,476,092 | B1 | * | 11/2002 | Kunita ........................ 522/31 |
| 2002/0055046 | A1 | * | 5/2002 | Ono et al. ................... 429/324 |
| 2004/0170890 | A1 |   | 9/2004 | Matsunaga et al. ......... 429/137 |

FOREIGN PATENT DOCUMENTS

EP    0095778 A1  *  12/1983
JP    2002-075443  *   3/2002

OTHER PUBLICATIONS

Matsumoto et al., Room temperature ionic liquids based on small aliphatic ammonium cations and asymmetric amide anions, Jul. 2, 2002, Chemical Communications 2002, pp. 1726-1727.*
Matsumoto et al., Physical and electrochemical properties of room temperature molten salt based on aliphatic onium cations and asymmetric amide anion, 2002, Electrochemical Society Proceedings, vol. 2002-19, pp. 1057-1065.*

* cited by examiner

*Primary Examiner* — Dah-Wei Yuan
*Assistant Examiner* — Angela J. Martin
(74) *Attorney, Agent, or Firm* — Ostrolenk Faber LLP

(57) ABSTRACT

There are provided a novel onium salt and a method for optimizing the interface of a negative electrode by the use of the novel onium salt and/or a conventional onium salt. Such a method is characterized in that an electrolyte comprising novel 2,2,2-trifluoro-N-(trifluoromethanesulfonyl) acetamide•tetraethyl ammonium salt is made to intervene between a negative electrode and a positive electrode in an electrochemical device having the constitution: a negative electrode|an electrolyte|a positive electrode, thereby constructing an electrode structure in the electrochemical device, and applying a voltage between the negative electrode and the positive electrode so as for the negative electrode to have a potential of −1 V to −5 V in terms of the potential relative to a reference electrode of $I^-/I^{3-}$, thereby forming a passive-state layer comprising a decomposition product of the above electrolyte or salt on the surface of the above negative electrode.

4 Claims, 1 Drawing Sheet

ONIUM SALT, ELECTROLYTE FOR NONAQUEOUS CELL CONTAINING THE NOVEL ONIUM SALT FOR NONAQUEOUS CELL AND METHOD FOR OPTIMIZING NEGATIVE ELECTRODE USING ELECTROLYTE CONTAINING ONIUM SALT

CROSS REFERENCE TO RELATED APPLICATIONS

The present application is a divisional of U.S. patent application Ser. No. 10/485,448, filed Jan. 29, 2004, which is a U.S.C. §371 National Phase conversion of PCT/JP02/07666 filed Jul. 29, 2002, which claims priority of Japanese Application No. 2001-231262 filed Jul. 31, 2001, Japanese Application No. 2001-335029 filed Oct. 31, 2001 and Japanese Application No. 2001-352963 filed Nov. 19, 2001, the entire contents of which are hereby incorporated by reference.

FIELD OF THE INVENTION

The present invention relates to a method of treating an electrode available for a primary or secondary lithium battery, and novel onium salt preferably used for a treating agent in such a method and useful for an ion liquid.

PRIOR ART

A solution prepared by dissolving an electrolyte in an organic solvent such as ethylene carbonate, propylene carbonate, dimethoxyethane, γ-butyrolactone, N,N-dumethylformamide, tetrahydrofuran, acetonitril and so forth has been used as a non-aqueous electrolyte for an electrochemical device such as a lithium primary battery, lithium secondary battery and so forth which has been used in recent years. Since, however, an organic solvent used for such electrolyte solutions is easy to volatilize and is a hazardous material itself, there have been problems in long-term reliability, durability and safety.

Accordingly, an application of onium salt in liquid state at ordinary temperature to electrolytes without using such organic solvents has been proposed and studied. For example, Unexamined Patent Publication (KoKai) No. 08-259543 describes that an onium salt comprising 1-ethyl-3-methylimidazorium cation and bistrifluoromethanesulfonimide anion is liquid at an ambient temperature and exhibits high ion conductivity.

WO 97/02252 Laying-open pamphlet describes an onium salt having as a cation a pyridinium ion, pyridazinium ion, pyrimidinium ion, pyrazinium ion, imidazolium ion, pyrazolium ion, thiazolium ion, oxazolium ion or triazolium ion which may be substituted, and as an anion non-Lewis acid containing polyvalent anion having 100 $Å^3$ and above of van der Waals volume and that such onium salts are non-hygroscopic ion liquid having a wide electrochemical window.

However, the onium salt having an aromatic cation such imidazolium cation and so forth as described above is easy to be reduced. For example, when a voltage of about −3.5V (reduction potential of lithium) in an $I^-/I^{3-}$ electrode system is applied, the onium salt is reduced. Therefore, there have been problems that charge and discharge by oxidation-reduction of lithium is unfeasible and such onium salts can not be used as electrolytes for a lithium battery. Further, there has been a problem that the ion conductivity of onium salt comprising a large cation and large anion generally lowers.

While WO97/02252 Laying-open pamphlet describes that the above-described salt described in said pamphlet, for example, 1,2-dimethyl-3-propylimidazolium•bis-(trifluoromethylsulfonil) imide dissolves well a lithium salt having the same kind of anions and is available for an electrolyte of rechargeable lithium ion battery, but does not verify such a thing. As a result of the present inventor's verification, it was confirmed as shown in Comparative Example 2 described later that when a potential of voltage of −3V and below in an $I^-/I^{3-}$ electrode system was applied, a cation of onium salt was irreversibly reduced and charge-discharge by oxidation-reduction of lithium could not be performed.

In studying practicability of a metal lithium electrode in an electrochemical device such as a lithium primary battery or lithium secondary battery, important things are not only search for optimum electrolytes, but also optimization of the interface between an electrode and electrolyte, that is, design of electrode structure. Since the reducing power of metal lithium is extremely strong, a thin passive-state layer originating from electrolyte is formed on the surface of metal lithium immediately when it comes into contact with electrolyte. By the presence of such a passive-state layer, a side reaction of a metal lithium negative electrode with electrolyte can be suppressed and an excessive activity on the surface of the negative electrode can be optimized.

Accordingly, the term "optimization of negative electrode" used herein is defined as that "a thin passive layer is formed mainly on the surface of a metal lithium negative electrode, which suppresses the side reaction of the metal lithium negative electrode with an electrolyte and optimizes an excessive activity on the surface of the negative electrode."

The definition or property or behavior of "a thin passive-state layer" will be described hereinafter in detail.

There has been conventionally proposed a method of optimizing a metal lithium negative electrode in order to attempt practical applications of the metal lithium negative electrode. At the present time, however, there is no onium salt suitable for optimizing the metal lithium negative electrode.

While a safe electrolyte available for applications other than a lithium battery has been highly required, there have been remarkably few onium salts known as being available as an electrolyte and the range of performance of such few onium salts is naturally restricted. Therefore, such requests have not been sufficiently realized. Since the performance required for electrolyte is generally different for each application, it has been a problem to discover numerous novel onium salts having performance suitable for each application in order to meet various demands for various kinds of performances such as ion conductivity, viscosity, resistance to reduction, resistance to oxidation, reactivity with water, melting point and so forth.

Problems to be Solved by Invention

Accordingly, a problem to be solved by the present invention is to provide a method of optimizing the interface of a negative electrode of an electrochemical device having the constitution: a negative electrode|an electrolyte|a positive electrode.

Another problem to be solved by the present invention is to provide an onium salt exhibiting an effect on a method of optimizing the interface of a negative electrode of an electrochemical device having the constitution: a negative electrode|an electrolyte|a positive electrode.

A further problem to be solved by the present invention is to provide a novel onium salt having characteristics superior to those of conventional onium salts.

Still more problem to be solved by the present invention is to provide electrolyte for non-aqueous-type electrochemical device containing a novel onium salt.

An additional problem to be solved by the present invention is to provide an electrochemical device using electrolyte for non-aqueous type electrochemical device containing a novel onium salt.

Other and further problems, features and advantages of the present invention will appear more fully from the following description taken in connection with the accompanying drawings.

Means for Solving the Problems

The above-described problems can be solved by a method of optimizing the interface of a negative electrode of an electrochemical device having the constitution: a negative electrode|an electrolyte|a positive electrode, comprising the steps of:

(a) making an electrolyte comprising a salt illustrated by the general formula (I);

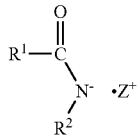

(I)

(wherein $R^1$ is a substituted or non-substituted mono-valent hydrocarbon group, $R^2$ is a mono-valent organic residue, and $Z^+$ is a mono-valent cation) to intervene between the positive electrode and the negative electrode, thereby constructing an electrode structure for an electrochemical device, and (b) applying a voltage between the positive electrode and the negative electrode so as for the negative electrode to have a potential of $-1\sim-5V$ in terms of the potential relative to a reference electrode of $I^-/I^{3-}$ to form a passive-state layer of a decomposition product of said electrolyte or salt on the surface of the negative electrode.

The above-described method of the present invention was achieved on the basis of the facts described below:

An experiment was carried out on the above-described present invention in order to measure cyclic voltammetery in the range of $0V\sim-3.6V$, using an iodine reference electrode in which a salt containing the above-described specific anion and a lithium ion was added into a conventional onium salt to prepare an electrolyte which was made to intervene between electrodes. Consequently, a discharge peak caused by dissolution of metal lithium which has been once deposited was observed. This fact means that a charge and discharge with oxidation-reduction of lithium is possible.

When an electrode which has been once treated in such a manner as above described is used, a charge-discharge with oxidation-reduction of lithium is feasible, even when only a conventional onium salt having low resistance to reduction is used without the salt illustrated by the above-described general formula (I) added therein.

The present inventors observed the surface of the negative electrode treated by the optimization method of the present invention with a scanning electron microscope. As a result, it was confirmed that the decomposition product of the onium salt illustrated by the above-described general formula (I) used as an electrolyte adheres to the surface of the negative electrode as particulate aggregates in a state of not dendrite, but stack of layers. Therefore, the following facts described below were confirmed:

In the optimization method of the present invention, by applying a voltage between the above-described negative electrode and positive electrode so as for the negative electrode to have a potential of $-1\sim-5V$ in terms of the potential relative to a reference electrode of $I^-/I^{3-}$, the onium salt illustrated by the above-described general formula (I) contained in the electrolyte decomposes to form on the surface of the negative electrode a passive-state layer having a property of transmitting not a cation of a conventional onium salt but a lithium ion. Direct contact of the onium salt illustrated by the above-described general formula (I) or onium salt having low resistance to reduction with the negative electrode can be suppressed by virtue of such a passive-state layer formed on the surface of the negative electrode, that is to say the interface between the negative electrode and the positive electrode. Therefore, these onium salts cannot be decomposed, that is these onium salts does not suffer non-reversible reduction, even if a high reduction voltage (negative voltage having larger absolute value) is applied. It is, accordingly, considered that the performances of these salts as electrolyte can be maintained.

The second problem of the present invention can be solved by an onium salt illustrated by the general formula (I');

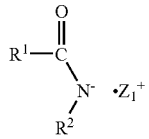

(I')

(wherein $R^1$ is a substituted or non-substituted mono-valent hydrocarbon group, $R^2$ is a mono-valent organic residue, and $Z^+$ is an organic onium ion other than pyridinium ion, pyridazinium ion, pyrimidinium ion, pyrazinium ion, imidazolium ion, pyrazolium ion, thiazolium ion, oxazolium ion and triazolium ion which may have a substituent) or an onium salt illustrated by the general formula (V);

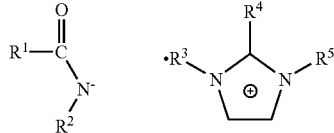

(V)

(wherein $R^1$ is a substituted or non-substituted mono-valent hydrocarbon group, $R^2$ is a mono-valent organic residue, and $R^3$, $R^4$ and $R^5$ are independently mono-valent organic residue having 1~8 carbon atoms)

These onium salts of the present invention are novel and have the characteristics that they are desirably available for a salt illustrated by the general formula (I) used in the aforementioned optimizing method of the present invention.

These novel onium salts of the present invention are different from conventional onium anions in that the former have a specific anion. That is to say, they have the characteristics that they have lower melting point and higher ion conductivity, compared with those of the conventional onium salt having the same kind of cations and different kind of anions. The onium salts illustrated by the general formula (V) are subsumed into the onium salts described in a published pamphlet of WO97/02252 in a broad sense. However, by selecting a combination of a specific cation with a specific anion from the onium salts described in a published pamphlet of WO97/02252, it is possible to obtain an onium salt ion having specifically high ion conductivity, despite the fact that the onium salt comprises a large cation and anion. Therefore, the onium salt of the present invention is excellent ion liquid in that its lower limit of the temperature range showing liquid state is low.

MOST PREFERRED EMBODIMENT FOR CARRYING OUT THE INVENTION

According to the method of the present invention, an electrolyte comprising the salt illustrated by the general formula (I) is made to intervene between a negative electrode and a positive electrodes to construct an electrochemical device, and then a voltage is applied between the positive electrode and the negative electrode so as for the negative electrode to have a potential of $-1\sim-5V$ in terms of the potential relative to a reference electrode of $I^-/I^{3-}$.

The $I^-/I^{3-}$ reference electrode is used herein only as a reference for expressing absolutely the voltage of the negative electrode. It is, therefore, naturally possible to use another reference electrode. However, when using another reference electrodes, the above-described voltage $-1\sim-5V$ must be converted to a voltage corresponding to such another reference electrodes.

In the present invention, the electrodes used for constituting the electrochemical device may be an electroconductive solid substance, but not specifically limited. It is, however, preferable to use an electroconductive solid substance having a melting point of 50° C. and above for reason that it hardly melts by exothermic heat when applying a voltage.

A combination of negative electrode with positive electrode preferably available in the present invention is exemplified by a combination for a lithium battery such as $Li/MnO_2$, $Li/(CF)_n$, $Li/CuO$, $C/LiCoO_2$, $Li/LiCoO_2$, $Li/LiMnO_4$, $LiAl/V_2O_5$, $LiAl/MnO_2$, $Li_2Nb_2O_5/V_2O_5$, $Li/Ag_2CrO_4$, $Li/FeS_2$, $Li/Bi_2O_3$, $Li/Bi_2Pb_2O_5$, $Li/P_2VP.nI_2$, $MnO_2/LiSiO_x$, $TiO_2/LiSiO_x$, $Li/LiFePO_4$, $Li/LiNiO_2$ and so forth.

The salt illustrated by the general formula (I) used in the method of the present invention is not specifically specified, so long as it is formed by the combination of a mono-valent cation and an acylamide anion illustrated by the general formula;

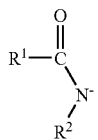

(wherein $R^1$ is a substituted or non-substituted mono-valent hydrocarbon group)

$R^1$ of the general formula (I) is not particularly specified so long as it is a substituted or non-substituted mono-valent hydrocarbon group. However, a substituted or non-substituted halogenated hydrocarbon group, particularly fluorine-substituted hydrocarbon group is preferable because its resistance to oxidation is high. The fluorine-substituted hydrocarbon group is exemplified by a fluoroalkyl group such as trifluoromethyl group, pentafluoroethyl group, heptafluoropropyl group, nonafluorobutyl group, heptafluoroisopropyl group, nonafluoroisobutyl group, 2,2,2-trifluoroethyl group, 1,1-difluoroethyl group, and so forth, fluoroaryl group such as pentafluorophenyl group, 2,4,6-trifluorophenyl group, and so forth, and fluoroaralkyl group such as heptafluorobenzyl group, 1,1-difluorobenzyl group and so forth. Above all, a straight-chain or branched-chain perfluoroalkyl group having 1~6 carbon atoms, perfluorophenyl group and perfluoroaralkyl group having 7-9 carbon atoms are particularly preferable because they are easily synthesized.

$R^2$ of the general formula (I) is not specifically specified so long as it is a mono-valent organic residue, and may be the same group as that illustrated by $\{R_1-C(=O)-\}$. However, a group having an electron attractive property having 1~6 carbon atoms, that is an electron attractive group, or a group having an electron attractive group is preferable because it is easily synthesized. The term "electron attractive group" used herein means a group having the Substituent Constant according to Hammett's law is higher than hydrogen atom. A mono-valent organic residue preferable for $R^2$ is exemplified by fluorinated hydrocarbon group (fluorine-substituted hydrocarbon group) such as fluoroalkyl group such as trifluoromethyl group, pentafluoroethyl group, heptafluoropropyl group, nonafluorobutyl group, heptafluoroisopropyl group, nonafluoroisobutyl group, 2,2,2-trifluoroethyl group, 1,1-difluoroethyl group and so forth, fluoroaryl group such as pentafluorophenyl group, 2,4,6-trifluorophenyl group and so forth, and fluoroaralkyl group such as heptafluorobenzyl group, 1,1-difluorobenzyl group, and so forth; an acyl group such as formyl group, acetyl group, propionyl group, butyryl group, isobutyryl group, valeryl group, isovaleryl group, pivaloyl group, lauroyl group and so forth; fluorinated acyl group (fluorin-substituted acyl group) such as trifluoroacetyl group, 2,2-difluoropropionyl group, perfluoropropionyl group, perfluorobutyryl group, perfluoroisobutyryl group, perfluorovaleryl group and so forth; substituted acyl group having a substituent other than fluorin such as methoxycarbonyl group, ethoxycarbonyl group, tert-butoxycarbonyl group, trifluoromethoxycarbonyl group, perfluoroethoxycarbonyl group, perfluoro-tert-butoxycarbonyl group and so forth; sulfonyl group such as methanesulfonyl group, ethanesulfonyl group, propanesulfonyl group, tert-butanesulfonyl group and so forth; fluorinated sulfonyl group (fluorine-substituted sulfonyl group) such as trifluoromethanesulfonyl group, pentafluoroethanesulfonyl group, heptafluoropropanesulfonyl group, nonafluorobutanesulfonyl group, heptafluoroisopropanesulfonyl group, nonafluoroisobutanesulfonyl group, 2,2,2-trifluoroethanesulfonyl group, 1,1-difluoroethanesulfonyl group and so forth; and fluorinated benzenesulfonyl group such as pentafluorobenzenesulfonyl group, 2,4,6-triflubenzenesulfonyl group and so forth.

An acylamide anion preferable for the salt illustrated by the general formula (I) is exemplified by sulfonylamide anion such as 2,2,2-trifluoro-N-(trifluoromethanesulfonyl)acetamide anion, 2,2,2-trifluoro-N-(perfluoroethanesulfonyl)acetamide anion, 2,2,2-trifluoro-N-(perfluoropropanesulfonyl)acetamide anion, 2,2,3,3,3-pentafluoro-N-(trifluoromethanesulfonyl)propioneamide anion, 2,2,3,3,3-pentafluoro-N-(perfluoroethanesulfonyl)propioneamide anion, 2,2,3,3,3-pentafluoro-N-(perfluoropropanesulfonyl) propioneamide anion, 2,2,3,3,4,4,4-heptafluoro-N-(trifluoromethanesulfonyl)butylamide anion, 2,2,3,3,4,4,4-heptafluoro-N-(perfluoroethanesulfonyl)butylamide anion, 2,2,3,3,4,4,4-heptafluoro-N-(perfluoropropanesulfonyl) butylamide anion and so forth; acylamide anion such as bistrifluoroacetamide anion, bis(3,3,3-trifluoropropione)imide anion, bis(perfluoropropione)imide anion, 2,2,2-trifluoro-N-(3,3,3-trifluoropropionyl)acetamide anion, 2,2,2-trifluoro-N-(perfluoropropionyl)acetamide anion and so forth; alkylamide anion such as 2,2,2-trifluoro-N-(trifluoromethyl)acetamide anion, 2,2,2-trifluoro-N-(2,2,2-trifluoroethyl)acetamide anion, 2,2,2-trifluoro-N-(perfluoroethyl) acetamide anion and so forth. Since the ion mobility of the onium salt containing the above-described anion increases as the ion becomes smaller, and a passive-state layer can be easily formed, 2,2,2-trifluoro-N-(trifluoromethanesulfonyl) acetamide anion, bis-trifluoroacetamide anion and 2,2,2-trifluoro-N-(trifluoromethyl)acetamide anion can be particularly preferably used.

The cation of the salt illustrated by the general formula (I), that is, $Z^+$ in the general formula (I) is not specifically specified, but is exemplified by an alkaline metal cation such as lithium cation, sodium cation, potassium cation and so forth, and an organic onium ion having at least one organic group formed by coordinating a cation type group with a compound containing an element having lone pair of electrons such as nitrogen, sulfur, oxygen, phosphorus, selenium, tin, iodine, antimony and so forth.

An organic omium ion preferably used in the present invention as a nitrogen-containing cation is exemplified by pyridinium ion, pyridazinium ion, pyrazinium ion, imidazolium ion, pyrazolium ion, triazolium ion, and a nitrogen-containing aromatic onium ion derived from these ion, as well as an ammonium cation illustrated by the following general formula (II)

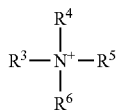
(II)

(wherein $R^3$, $R^4$, $R^5$ and $R^6$ are independently mono-valent organic residue having 1~8 carbon atoms respectively, each of $R^3$ and or $R^5$ and $R^6$ can bond with each other to form a non-aromatic ring.)

$R^3$, $R^4$, $R^5$ and $R^6$ in the above-described general formula (II) are independently mono-valent organic residue having 1~8 carbon atoms respectively. The organic residue is not limited to a hydrocarbon group, but may contain a hetero atom in such a form as ether linkage, thioether linkage, and so forth. However, an alkyl group or alkenyl group having 1 to 8 carbon atoms, particularly 1 to 3 carbon atoms is preferable because of easiness of synthesize. Each of $R^3$ and $R^4$, or $R^5$ and $R^6$ can bond with each other to form a non-aromatic ring. Such a ring is preferably an aliphatic ring.

Preferable examples of the nitrogen-containing aromatic organic onium ion are a symmetric imidazolium cation such as 1,3-dimethylimidazolium cation, 1,3-diethylimidazolium cation, 1,3-dipropylimidazolium cation, 1,3-dipropylimidazolium cation and so forth; an unsymmetrical imidazolium cation such as 1-ethyl-3-methylimidazolium cation, 1-methyl-3-propylimidazolium cation, 1-isopropyl-3-propylimidazolium cation, 1-tert-butyl-3-isopropylimidazolium cation and so forth; and pyridinium cation such as N-ethylpyridinium cation, N-butylpyridinium cation and so forth.

Preferable examples of the ammonium cation illustrated by the general formula (II) are a symmetric ammonium cation such as tetramethylammonium cation, tetraethylammonium cation, tetrapropylammonium cation, and so forth; an ammonium cation in which the number of carbon of the shortest substituent is not less than 50 percent and less than 100 percent of the that of the longest substituent (hereinafter may be referred to as "pseudosymmetric") such as ethyltrimethylammonium cation, vinyltrimethylammonium cation, triethylmethylammonium cation, triethylpropylammonium cation, diethyldimethylammonium cation, tributylethylammonium cation, triethylisopropylammonium cation, N,N-dimethylpyrrolidinium cation, N-methyl-N-ethylpyrrolidinium cation, triethylmethoxymethylammonium cation, and so forth; an unsymmetric ammonium cation such as triemethylpropylammonium cation, triemethylisopropylammonium cation, butyltriemethylammonium cation, allyltriemethylammonium cation, hexyltriemethylammonium cation, octyltriemethylamronium cation, dodecyltriemethylammonium cation, trieethylmethoxyethoxymethylammonium cation, dimethyldipropylammonium cation and so forth; a di-valent ammonium cation such as hexamethonium cation and so forth; an aliphatic monocyclic ammonium cation such as N-methyl-N-propylpyrrolidinium cation, N-methyl-N-ethylpiperidinium cation and so forth; and an aliphatic multicyclic ammonium cation such as N,N-tetramethylenepyrrolidinium cation, N–N-hexamethylenepyrrolidinium cation, N, N-hexamethylenepiperidinium cation and so forth.

A phosphorus-containing cation is exemplified by a non-aromatic phosphonium cation illustrated by the general formula (III);

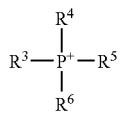
(III)

(wherein $R^3$, $R^4$, $R^5$ and $R^6$ are the same as those defined in the general formula (II) respectively.)

Preferable examples of the phosphonium cation are symmetric phosphonium cation such as tetramethylphosphonium cation, tetraethylphosphonium cation, tetrapropylphosphonium cation, tetrabutylphosphonium cation, tetraoctylphosphonium cation, tetraphenylphosphonium cation, and so forth; pseudosymmetic phosphonium cation such as trimethylethylphosphonium cation, triethylmethylphosphonium cation, and so forth; unsymmetric phosphonium cation such as hexyltrimethylphosphonium cation, trimethyloctylphosphonium cation and so forth; aliphatic cyclic phosphonium cation such as P,P-diethylphosphoranium cation, P-methyl-P-ethylphosphinanium cation, P,P-tetramethylenephosphoranium cation and so forth.

A sulfur atom-containing cation is exemplified by a sulfonium cation illustrated by the general formula (IV);

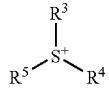
(IV)

(wherein $R^3$, $R^4$ and $R^5$ are independently mono-valnet organic residue, $R^3$ and $R^4$ can bond to form a ring). Each of $R^3$, $R^4$ and $R^5$ in the above-described general formula (IV) is independently mono-valent organic residue having 1~8 carbon atoms. The organic residue is not limited to a hydrocarbon group, but may contain a hetero atom in such a form as ether linkage, thioether linkage and so forth. However, an alkyl group or alkenyl group having 1 to 8 carbon atoms, particularly 1 to 3 carbon atoms is preferable because of easiness of synthesis. $R^3$ and $R^4$ in the above-described general formula (IV) can bond to form a ring which is preferably an aliphatic ring. Preferable examples of the sulfonium cation illustrated by general formula (IV) are symmetric sulfonium cation such as trimethylsulfonium cation, triethylsulfonium cation, tributylsulfonium cation and so forth; pseudosymmetric sulfonium cation such as diethylmethylsulfonium cation and so forth; unsymmetrical sulfonium cation such as dimethylpropylsulfonium cation, dimethylhexylsulfonium cation and so forth; aliphatic cyclic sulfonium cation such as S-ethyltetrahydrothiopyranium cation, S-butyltetrahydrothiophenium cation and so forth.

As an organic onium ion preferably used other than those described above may be an aromatic organic onium ion such as thiazolium ion, oxazolium ion and so forth.

In particular, lithium cation, symmetric ammonium cations, pseudoammonium cations, symmetric imidazolium cations, non-symmetric imidazolium cations, aliphatic monocyclic ammonium cations, aliphatic multicyclic ammonium cations, and aliphatic cyclic phosphonium cations may be preferably used. This is because that they are hardly affected by impurities originated from the treatment for electrode when using for a lithium battery. When using the salt illustrated by the general formula (I) in which the cation is a cation other than a metal cation such as a lithium cation and so forth, it is preferable to use a salt having a metal cation, particularly a lithium cation additionally from the standpoint of effect.

In the salts illustrated by the above-described general formula (I) used in the treating method of the present invention, an organic onium salt having a cation which is other than pyridinium ion, pyridazinium ion, pyrimidinium ion, pyrazinium ion, imidazolium ion, pyrazolium ion, thiazolium ion, oxazolium ion or triazolium ion which may have a substituent; that is, an onium salt illustrated by the general formula (I');

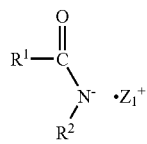

(I')

(wherein $R^1$ is a substituted or non-substituted mono-valent hydrocarbon group, $R^2$ is a mono-valent organic residue, and $Z^+$ is an organic onium ion, provided that pyridinium ion, pyridazinium ion, pyrimidinium ion, pyrazinium ion, imidazolium ion, pyrazolium ion, thiazolium ion, oxazolium ion and triazolium ion which may have a substituent are excluded) is a novel compound.

In particular, a salt having a cation ($Z_1^+$) which is "an organic onium ion other than an organic onium ion originating from an aromatic hetero five-membered or six-membered ring compound having at least one selected from the group consisting of N, S and O" is preferable, because it has a low melting point and is liquid at a low temperature and can be used itself as non-aqueous electrolyte without the use of an organic solvent. Among them, $Z_1^+$ is particularly preferably an ammonium cation, phosphonium cation or sulfonium cation illustrated by the above-described general formulae (II)~(IV). This is because that it has lower melting point than an onium salt having the same cation as that of the present invention, but different anion from that of the present invention and has wide range of temperatures at which it is used as non-aqueous electrolyte. The onium salt illustrated by the general formula (V) among the salts illustrated by the above-mentioned general formula (I):

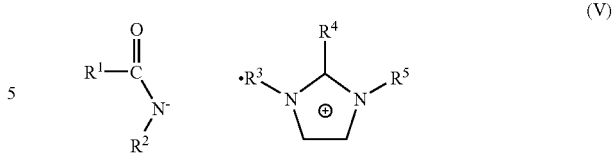

(V)

[wherein each of $R^1$ and $R^2$ has the same meaning as those of $R^1$ and $R^2$ of the above-mentioned general formula (I), and each of $R^3$, $R^4$ and $R^5$ is independently mono-valent organic residue having 1~8 carbon atoms] has characteristics that not only has it lower melting point similarly to the onium salt illustrated by the above-described general formula (I'), but also has it significant high ion conductivity compared with the onium salt having the other anion such as bis-(trifluoromethylsulfonyl) imide and so forth, despite the fact that it has as a cation an organic onium ion originating from an aromatic hetero five-membered compound having nitrogen atom.

In the above-described general formula (V), each of $R^1$ and $R^2$ has the same meaning as those of $R^1$ and $R^2$ of the above-mentioned general formula (I), and each of $R^3$, $R^4$ and $R^5$ is independently mono-valent organic residue having 1~8 carbon atoms. The organic residue is not restricted to a hydrocarbon group, but may contain a hetero-atom in a form of ether linkage, thioether linkage, etc. However, the organic residue is preferably an alkyl group or alkenyl group having 1~8 carbon atoms, especially 1~3 carbon atoms. Preferable examples of the onium salt illustrated by the above-described general formula (V) are symmetrical imidazolium cations such as 1,3-dimethyl imidazolium cation, 1,3-diethyl imidazolium cation, 1,3-dipropyl imidazolium cation and so forth; non-symmetrical imidazolium cations such as 1-ethyl-3-methyl imidazolium cation, 1-methyl-3-propyl imidazolium cation, 1-isopropyl-3-propylimidazolium cation, 1-tert-butyl-3-isopropyl imidazolium cation, etc.

These novel onium salts can be easily prepared by a salt-exchange method in which an acylamide anion metal salt illustrated by the general formula (VI)

(VI)

[wherein, each of $R^1$ and $R^2$ has the same meaning as those of $R^1$ and $R^2$ of the above-mentioned general formula (I), and M represents a metal element] is mixed with an organic onium ion halogen salt. When the onium salt illustrated by the above-described general formula (I') is prepared, a halogen salt of corresponding organic onium ion is used as an organic onium ion halogen salt. When the onium salt illustrated by the above-described general formula (V) is prepared, $R^1$ and $R^2$ which are corresponding to each anion are selected and a halogen salt of corresponding imidazolium ion is used as an organic onium ion halogen salt.

A metal preferably used for a metal salt of acylamide anion used in the above-described salt-exchange method, that is, M in the above-described general formula (VI) is, for example, alkaline metal such as lithium, sodium, potassium and so forth or alkaline earth metal such as magnesium, calcium and so forth. Above all, an alkaline metal such as lithium, sodium, potassium and so forth may be preferably used from the view point of easiness of ion-exchange. Potassium is most preferably used, because the hygroscopicity of the metal salt as raw material is low and the purity of the metal salt can be easily increased by recrystallization.

These metal salts can be easily synthesized in such a manner as described below. That is to say, amine illustrated by the general formula (VII)

$$R^2\text{---}NH_2 \quad (VII)$$

[wherein, $R^2$ has the same meaning as that of $R^2$ of the above-mentioned general formula (I)] is reacted with a metal salt dehydrogenation agent such as metal alkoxide and so froth, and then is reacted with acid anhydride illustrated by the general formula (VIII)

$$R^1\text{---}C(=O)\text{---}O\text{---}C(=O)\text{---}R^1 \quad (VIII)$$

[wherein, $R^1$ has the same meaning as that of $R^1$ of the above-mentioned general formula (I)]

While halogen of organic onium halogen salt used for salt-exchange method is not restricted, chlorine, bromine or iodine is preferably used for easiness of the salt-exchange method. It is more preferable to select halogen belonging to the same period of the periodic table as that of metal salt of acylamide anion for easiness of removal of inorganic salt, a by-product after the salt-exchange method.

The salt-exchange method is usually carried out in solvent. The solvent is not particularly restricted. Examples of the solvent are organic solvents such as halogenated hydrocarbon such as chloroform, dichloromethane and so forth; ether such as diisopropyl ether, diethyl ether, tetrahydrofuran, 1,4-dioxane and so forth; ketone such as acetone, methyl ethyl ketone and so forth; ester such as ethyl acetate, isopropyl acetate and so forth; nitrile such as acetonitrile and so forth; alcohol such as methanol, ethanol, isopropyl alcohol, tert-butyl alcohol and so forth; amide such as dimethylformamide, dimethylacetamide, and so forth; sulfoxide such as dimethyl suboxide and so forth; and water. Particularly, solvents such as acetone, methyl ethyl ketone, acetonitrile, methanol, ethanol, isopropyl alcohol, tert-butyl alcohol, dimethylformamide, dimethylacetamide, dimethyl sulfoxide and water having the relative dielectric constant of 10 and above are preferably used. This is because that the solubilities of metal salt of acylamide anion and halogen salt of organic cation as raw materials in such solvents are high.

The conditions for salt exchange reaction is not particularly restricted, but can be carried out under heating, cooling, pressure, reduced pressure or normal pressure. The salt exchange reaction proceeds sufficiently within 10 hours. After completion of the salt exchange reaction, inorganic by-products are removed to isolate an objective product. The objective product can be easily isolated from by-products by, for example, a method in which an inorganic salt is extracted in aqueous phase, thereafter solvent is removed, a method in which an inorganic salt is deposited and filtered, thereafter solvent is removed, a method in which an inorganic salt is dissolved and the objective product is crystallized, thereafter filtered. When the isolated onium salt contains moisture, drying the onium salt can be carried out by concentration or azeotropic distillation, if necessary.

Since the onium salt of the present invention thus obtained has usually a low melting point and high ion conductivity, it is preferably used for electrolyte for a primary or secondary lithium ion or lithium metal battery, electrolyte for a dye-sensitizing solar cell, electrolyte for capacitor, electrolyte for electrochromic display material, electrolyte for plating, solvent for reaction and so forth.

When the onium salt of the present invention is used for such uses as above described, one type of the onium salt of the present invention can be used singly, or two or more types of the onium salt of the present invention can be used in mixture.

It is, further, possible to mix the onium salt of the present invention with another salt such as conventional onium salt etc., or solvent.

When using the onium salt of the present invention with another salt or solvent mixed, it is possible to increase the resistance to electrochemical reduction, compared with another salt or solvent without the onium salt of the present invention. For example, by adding the onium salt of the present invention into an electrolyte having the reduction potential lower than that of lithium, the electrolyte is made possible to use such an electrolyte as a primary and secondary lithium ion and lithium metal battery. Further, by constituting an electrochemical device such as lithium battery, dye-sensitizing solar cell, capacitor, electrochromic display material and so forth by the use of an electrolyte comprising onium salt of the present invention, it is possible to constitute an electrochemical device having excellent low temperature characteristics.

According to the present invention, a battery is composed by making an electrolyte containing the salt illustrated by the general formula (I) to intervene between such a pair of electrodes as described above, and a given voltage is applied. The method for making the above-described electrolyte to intervene between electrodes is not particularly restricted, provided that the portion of the electrodes which comes in contact with an electrolyte can contact at least the electrolyte containing the above-described salt in actual use. For example, the above-described electrolyte may be made to intervene between a pair of electrodes in the molten state or can be made to intervene between a pair of electrodes as an electrolyte prepared by mixing the above-described electrolyte with solvent or another salt (electrolyte). At this time, the electrolyte containing the above-described salt is not necessarily present only between a pair of electrodes, but a pair of electrodes may be dipped in the electrolyte. When the electrolyte containing the salt illustrated by the general formula (I) is used as a mixture with solvent or another electrolyte, the concentration of the salt in the electrolyte is preferable 0.001 weight % and above, and more preferably 0.1~50 weight % in consideration of making use of characteristics of another electrolyte.

An additive such as a metal fluoride layer-forming agent such as HF and so forth, an alloy layer-forming agent such as $AlI_3$, $MgI_2$, $SnI_2$ and so forth, a protective layer-forming agent such as $S_x^{2-}$ and forth, an organic additives such as 2-mechylfuran, 2-methyltetrahydrofuran, pyridine derivative, dipyridyl derivative, cetyltrimethylammonium and so forth, and gas-additive such as $CO_2$, $NO_2$, $CO$ and so forth can be preferably added to the electrolyte containing the salt illustrated by the general formula (I), because of easiness of controlling the composition, thickness or shape of the passive-state layer formed on the surface of negative electrode. The amount of addition of such additives are properly determined in consideration of various kinds of conditions such as the composition and properties of electrolyte, combination of electrode, the composition, thickness and shape of the passive-state layer to be formed on the surface of negative electrode and so forth.

According to the present invention, it is necessary to apply between the above-described pair of electrodes such a voltage that an electric potential of the negative electrode becomes $-1\sim5V$ represented by an electric potential when using $I^-/I^{3-}$ as a reference electrode. When such a voltage that produces such range of electric potential is not applied, the effects of the present invention can not be obtained. However the electric potential of the negative electrode is excessively higher, a treatment for a long term of period is required in order to obtain the desired effects. On the contrary, when the electric potential of the negative electrode is excessively lower, the effects obtained are often lowered. Therefore, an electric potential of $-1.5\sim-4.0V$ represented by an electric potential when using I−/I$_3^-$ as a reference electrode is preferable. From the standpoint of high efficiency of charge-discharge by oxidation-reduction when using a lithium battery, an electric potential of −2.0~−3.5V represented by an electric potential of I−/I$_3^-$ reference electrode is particularly preferable. The temperature of the electrolyte and applying time when a voltage is applied are determined properly depending upon the types of the electrolytes used and voltage applied. It is, however, preferable that the temperature of the electrolyte is −30~200° C. and the applying time is usually 1 m second~10 hours. Application of voltage may be carried out at one time or separately.

The treatment of electrodes according to the treatment method of the present invention can be carried out as a part of manufacturing process of electrode before using the electrodes in each of uses, but can be carried out at the time when the electrodes are used in each of uses. For example, when the electrode is used as a lithium-secondary battery, a method can be adopted in which the salt illustrated by the general formula (I) is added in the electrolyte for the battery, then the electrode is subjected to the treatment of the present invention at the time of charging, and is used intact as a battery. In such a method, when an electrolyte comprising an onium salt such as 1-ethyl-3-methylimidazorium bis-trifluoromethane sulfonamide etc., which is liquid state at ordinary temperatures or an electrolyte containing only the salt illustrated by the general formula (I) which is liquid state at ordinary temperatures is used as an electrolyte to which the salt illustrated by the general (I) is added, the afore-mentioned problem of safety can be solved.

The present invention will be understood more readily with reference to the following examples; however these examples are intended to illustrate the invention and are not to be constructed to limit the scope of the invention.

EXAMPLE

Production Example 1

According to the following method, potassium salt of 2,2, 2-trifluoro-N-(trifluoromethane sulfonyl)acetamide was prepared as a metal salt of acylamide anion used for production of an onium salt of the present invention by means of salt-exchange method.

To a 1000 ml three-necked flask equipped with a thermometer, dropping funnel and nitrogen balloon, 69.42 g (0.4656 mol) of trifluoromethanesulfoneamide were added, and 500 ml of dehydrated methanol were added to dissolve trifluoromethanesulfoneamide, and then 52.25 g (0.4656 mol) of tert-butoxypotassium were added to proceed with the reaction at 60° C. for three hours to prepare a solution. Thereafter, the solution was concentrated under reduced pressure to obtain white powder. Then, 250 ml of dehydrated diethyl ether were added to the white powder to obtain slurry. After cooling the slurry to 0° C., to which were added dropwise a mixed solution of 97.80 g (0.4656 mol) of trifluorobutyric acid anhydride and 250 ml of dehydrated diethylether to obtain a solution. The solution thus obtained was stirred at 0° C. for two hours and reacted at room temperature for four hours. Then, the slurry thus obtained was cooled, filtered, and washed with diethylether to obtain a crystal. The crystal thus obtained was dried under reduced pressure to obtain 116.75 g (88.5% yield) of white powder.

10~20 mg of white powder thus obtained were dissolved in about 1 ml of dimethylsulfoxide (containing 1,4-bistrifluoromethylbenzene as a standard substance) and $^1$H and $^{19}$F nuclei were measured by nuclear magnetic resonance "JNM-LA500" (trade name) manufactured by NIHON DENSHI Co. LTD. As a result, no peak was observed in $^1$H-NMR, but two singlet peaks were observed in $^{19}$F-NMR, one is −76.69 ppm (3F) and the other is −80.24 ppm (3F). The peak position of $^{19}$F showed chemical shift in the case where the peak of 1,4-bistrifluoromethylbenzene is taken as −63.75 ppm. Further, by MS-ESI (solvent: methanol) measurement, an anion having a molecular weight of 244.0 which is considered as $CF_3CONSO_2CF_3^-$ ion was observed. It was confirmed by the above-described measurements that the objective metal salt was synthesized.

Production Example 2

The same procedures as those of production example 1 were repeated, except that pentafluoroethanesulfoneamide was used instead of trifluoromethanesulfoneamide to prepare potassium salt of 2,2,2-trifluoro-N-(pentafluorosulfonyl)acetamide.

Production Example 3

The same procedures as those of production example 1 were repeated, except that methanesulfoneamide was used instead of trifluoromethanesulfoneamide to prepare potassium salt of 2,2,2-trifluoro-N-(methanesulfonyl)acetamide.

Production Example 4

The same procedures as those of production example 1 were repeated, except that trifluoroacetamide was used instead of trifluoromethanesulfoneamide to prepare potassium salt of bis-trifluoroacetylimide.

Example 1

14.16 g (50 mmol) of potassium salt of 2,2,2-trifluoro-N-(trifluoromethane sulfonyl) acetamide produced in Production Example 1 and 7.58 g (50 mmol) of triethylmethylammonium chloride were weighed in atmosphere of nitrogen under the relative humidity of 10% and below in a gloved box and dissolved in 50 ml of ion-exchanged water to separate in two phases. 100 ml of methylene chloride were added to the mixed solution and extracted to obtain an organic phase. The organic phase was washed twice with 50 ml of ion-exchanged water. The organic phase thus obtained was concentrated under reduced pressure to obtain 14.31 g of {2,2,2-trifluoro-N(trifluoromethanesulfonyl)acetamide triethylmethylammonium salt} in a state of colorless, transparent and liquid. NMR measurement was made on the solution similarly to Production Example 1. Results obtained were as follows:

$^1$H-NMR: 1.21 ppm(t), 2.89 ppm(s), 3.26 ppm(q)
$^{19}$F-NMR: −76.70 ppm(s), −80.23 ppm(s)

The solution was analyzed by a differential thermal calorimeter (DSC) to obtain melting point of 11.1° C. The ion conductivity of the solution was measured at 25° C. to obtain 4.3 mS/cm.

Comparative Example 1

The same procedures as those of Example 1 were repeated, except that lithium salt of bis trifluoromethanesulfone imide was used instead of potassium salt of 2,2,2-trifluoro-N-(trifluoromethanesulfonyl)acetamide to prepare onium salt, and bis (trifluoromethanesulfonyl)imide triethyl methyl ammonium salt was obtained. NMR measurement was made on the salt. Results obtained were as follows:

$^1$H-NMR: 1.21 ppm(t), 2.89 ppm(s), 3.26 ppm(q)
$^{19}$F-NMR: −80.59 ppm(s)

The salt obtained was analyzed by a differential thermal calorimeter (DSC) to obtain melting point of 98.0° C. Since the salt was solid at a temperature of 25° C., ion-conductivity could not be measured.

Examples 2-13

The same procedures as those of Example 1 were repeated, except that compounds shown in Tables 1~3 were used as raw materials instead of triethylmethylammonium chloride to obtain compounds shown in Table 1~3. With respect to the onium salt thus obtained, results of NMR analysis, melting point and ion-conductivity at 25° C. were shown in Table 1~3. In Tables, a symbol "–" in the column "ion-conductivity" means that measurement could not be made because of being solid at 25° C. It was confirmed that the onium slat obtained exhibits ion-conductivity in a molten state.

Examples 14~18

The same procedures as those of Example 1 were repeated, except that compounds shown in Tables 4~5 were used as raw materials instead of triethylmethylammonium chloride to obtain compounds shown in Table 4~5. With respect to the onium salt thus obtained, results of NMR analysis, melting point and ion-conductivity at 25° C. were shown in Tables 4~5. In Tables, a symbol "–" in the column "ion-conductivity" means that measurement could not be made because of being solid at 25° C. It was confirmed that the onium slat obtained exhibits ion-conductivity in a molten state.

TABLE 1

| example | raw material | product | NMR (ppm) | melting point (° C.) | ion conductivity (mS/cm) |
|---|---|---|---|---|---|
| 2 | tetramethyl ammonium bromide | 2,2,2-trifluoro-N-(trifluoromethanesulfonyl) acetamide tetramethylammonium salt | $^1$H-NMR: 3.12(s) $^{19}$F-NMR: −76.69(s), −80.23(s) | 64 | — |
| 3 | tetraethylammonium bromide | 2,2,2-trifluoro-N-(trifluoromethanesulfonyl) acetamide tetraethylammonium salt | $^1$H-NMR: 1.17(t), 3.22(q) $^{19}$F-NMR: −76.69(s), −80.23 s) | 23 | 3.9 |
| 4 | tetrapropylammonium bromide | 2,2,2-trifluoro-N-(trifluoromethanesulfonyl) acetamide tetrapropylammonium salt | $^1$H-NMR: 0.92(t), 3.00(m), 3.63(m) $^{19}$F-NMR: −76.69(s), −80.23(s) | 82 | — |
| 5 | trimethylisopropyl ammonium iodide | 2,2,2-trifluoro-N-(trifluoromethanesulfonyl) acetamide trimethylisopropylammonium salt | $^1$H-NMR: 1.31(d), 3.29(s), 3.15(m) $^{19}$F-NMR: −76.69(s), −80.23(s) | 24 | 2.8 |

TABLE 2

| example | raw material | product | NMR (ppm) | melting point (° C.) | ion conductivity (mS/cm) |
|---|---|---|---|---|---|
| 6 | hexyltrimethyl ammonium bromide | 2,2,2-trifluoro-N-(trifluoromethanesulfonyl) acetamide hexyltrimethylammonium salt | $^1$H-NMR: 0.89(t), 1.31(m), 1.68(m), 3.05(s), 3.28(t) $^{19}$F-NMR: −76.69(s), −80.23(s) | −76 (Tg) | 1.5 |
| 7 | trimethyloctyl ammonium bromide | 2,2,2-trifluoro-N-(trifluoromethanesulfonyl) acetamide trimethyloctylammonium salt | $^1$H-NMR: 0.87(t), 1.28(m), 1.68(m), 3.05(s), 3.28(t) $^{19}$F-NMR: −76.69(s), −80.23(s) | −72 (Tg) | 1.0 |
| 8 | triethylmethoxy ethoxymethyl ammonium chloride | 2,2,2-trifluoro-N-(trifluoromethanesulfonyl) acetamide triethylmethoxyethoxymethyl ammonium salt | $^1$H-NMR: 1.20(t), 3.24(q), 3.53(t), 3.88(t), 4.65(s) $^{19}$F-NMR: −76.69(s), −80.23(s) | −83 (Tg) | 3.9 |
| 9 | 1,3-dimethyl imidazolium iodide | 2,2,2-trifluoro-N-(trifluoromethanesulfonyl) acetamide 1,3-dimethylimidazolium salt | $^1$H-NMR: 3.86(s), 7.70(s), 9.12(s) $^{19}$F-NMR: −76.69(s), −80.23(s) | 34 | — |

TABLE 3

| example | raw material | product | NMR (ppm) | melting point (° C.) | Ion conductivity (mS/cm) |
|---|---|---|---|---|---|
| 10 | 1-ethyl-3-methyl imidazolium bromide | 2,2,2-trifluoro-N-(trifluoromethanesulfonyl) acetamide 1-ethyl-3-methylimidazolium salt | $^1$H-NMR: 1.43(t), 3.86(s), 4.20(q), 7.70(s), 7.79(s), 9.12(s) $^{19}$F-NMR: −76.69(s), −80.23(s) | 3 | 9.8 |
| 11 | 1,3-diisopropyl imidazolium iodide | 2,2,2-trifluoro-N-(trifluoromethanesulfonyl) acetamide 1,3-diisopropylimidazolium salt | $^1$H-NMR: 1.50(d), 4.63(m), 7.93(s), 9.27(s) $^{19}$F-NMR: −76.69(s), −80.23(s) | 34 | — |
| 12 | hexamethonium dibromide | 2,2,2-trifluoro-N-(trifluoromethanesulfonyl) acetamide hexamethonium salt | $^1$H-NMR: 1.33(m), 1.71(m), 3.06(m), 3.27(m) $^{19}$F-NMR: −76.69(s), −80.23(s) | 51 | — |
| 13 | N,N-tetramethylene pyrrolidinium iodide | 2,2,2-trifluoro-N-(trifluoromethanesulfonyl) acetamide N,N-tetramethylene pyrrolidinium salt | $^1$H-NMR: 2.08(m), 3.49(m) $^{19}$F-NMR:−76.69(s), −80.23(s) | 15 | 6.5 |

TABLE 4

| example | raw material | product | NMR (ppm) | melting point (°C.) | ion conductivity (mS/cm) |
|---------|--------------|---------|-----------|---------------------|--------------------------|
| 14 | tetraethyl phosphonium bromide | 2,2,2-trifluoro-N-(trifluoromethanesulfonyl) acetamide tetraethylphosphonium salt | $^{1}$H-NMR: 1.15(m), 2.23(m)  $^{19}$F-NMR: −76.69(s), −80.21(s) | 19 | 5.3 |
| 15 | tetrabutyl phosphonium bromide | 2,2,2-trifluoro-N-(trifluoromethanesulfonyl) acetamide tetrabutylphosphonium salt | $^{1}$H-NMR: 0.92(t), 1.45(m), 2.19(m)  $^{19}$F-NMR: −76.69(s), −80.21(s) | 40 | — |
| 16 | tetraoctyl phosphonium bromide | 2,2,2-trifluoro-N-(trifluoromethanesulfonyl) acetamide tetraoctylphosphonium salt | $^{1}$H-NMR: 0.87(t), 1.38(m), 2.17(m)  $^{19}$F-NMR: −76.69(s), −80.21(s) | 10 | 0.1 |

TABLE 5

| example | raw material | product | NMR (ppm) | melting point (°C.) | ion conductivity (mS/cm) |
|---------|--------------|---------|-----------|---------------------|--------------------------|
| 17 | tetraphenyl phosphonium bromide | 2,2,2-trifluoro-N-(trifluoromethanesulfonyl) acetamide tetraphenylphosphonium salt | $^{1}$H-NMR: 7.76(m), 7.83(m), 7.98(m)  $^{19}$F-NMR: −76.69(s), −80.21(s) | 130 | — |
| 18 | trimethylsulfonium bromide | 2,2,2-trifluoro-N-(trifluoromethanesulfonyl) acetamide trimetylsulfonium salt | $^{1}$H-NMR: 2.85(m)  $^{19}$F-NMR: −76.69(s), −80.21 (s) | 32 | — |

Production Examples 19~20

The same procedures as those of Example 1 were repeated, except that compounds shown in Table 6 were used as acylamide anion materials instead of 2,2,2-trifluoro-N-(trifluoromethanesulfonyl)acetamide potassium salt and compounds shown in Table 6 were used as cation materials instead of triethylmethyl ammonium chloride to obtain compounds shown in Table 6. The ion-conductivity of the onium salt was shown in Table 6.

parent liquid (bistrifluoroacetylimide triethylmethylammonium salt). Results of NMR analysis on the liquid were as follows:

$^{1}$H-NMR: 1.21 ppm (t), 2.89 ppm(s), 3.26 ppm(q)

$^{19}$F-NMR: −91.12 ppm(s)

The liquid was analyzed by a differential thermal calorimeter (DSC) to obtain melting point of 10.9° C. The ion conductivity of the liquid was measured at 25° C. to obtain 5.8 mS/cm.

TABLE 6

| example | acylamideanion raw material | cation raw material | product | NMR (ppm) | ion conductivity (mS/cm) |
|---------|------------------------------|---------------------|---------|-----------|--------------------------|
| 19 | 2,2,2-trifluoro-N-(pentafluoroethanesulfonyl) acetamide potassium salt | 1-ethyl-3-methyl imidazolium bromide | 2,2,2-trifluoro-N-(pentafluoroethanesulfonyl) acetamide 1-ethyl-3-methylimidazolium salt | $^{1}$H-NMR: 1.43(t), 3.86(s), 4.20(q), 7.70(s), 7.79(s), 9.12(s)  $^{19}$F-NMR: −76.69(s), −81.75(q), −89.47(t) | 8.5 |
| 20 | 2,2,2-trifluoro-N-(methanesulfonyl) acetamide potassium salt | 1-ethyl-3-methyl imidazolium bromide | 2,2,2-trifluoro-N-(methanesulfonyl) acetamide 1-ethyl-3-methylimidazolium salt | $^{1}$H-NMR: 1.43(t), 2.81(s), 3.86(s), 4.20(q), 7.70(s), 7.79(s), 9.12(s)  $^{19}$F-NMR: −76.71(s) | 3.1 |

Example 21

12.36 g (50 mmol) of potassium salt of bistrifluoroacetylimide produced Production example 4 and 7.58 g (50 mmol) of triethylmethylammonium chloride were weighed in an atmosphere of nitrogen under the relative humidity of 10% and below in a gloved box and dissolved in 50 ml of acetonitrile to form white slurry. The slurry thus obtained was filtered under pressurized nitrogen and washed with 10 ml of acetonitrile. A mixture of filtrate and wash liquid was concentrated under reduced pressure to obtain 14.59 g of colorless, trans- Examples 22~31

The same procedures as those of Example 21 were repeated, except that compounds shown in Tables 7 and 8 were used instead of triethylmethylammonium chloride to obtain compounds shown in Tables 7 and 8. Results of NMR analysis for onium salt obtained, melting point, and ion-conductivity of onium salt in liquid state at 25° C. were shown in Tables 7 and 8. In Tables, a symbol "−" in the column "ion-conductivity" means that measurement could not be made because of being solid at 25° C. It was confirmed that the onium slat obtained exhibits ion-conductivity in a molten state.

TABLE 7

| example | raw material | product | NMR (ppm) | melting point (° C.) | Ion conductivity (mS/cm) |
|---|---|---|---|---|---|
| 22 | tetramethyl ammonium bromide | bistrifluoroacetylimide tetrametylammonium salt | $^1$H-NMR: 3.12(s)<br>$^{19}$F-NMR: −76.65(s) | 104 | — |
| 23 | tetraethyl ammonium bromide | bistrifluoroacetylimide tetraethylammonium salt | $^1$H-NMR: 1.17(t), 3.22(q)<br>$^{19}$F-NM: −76.65(s) | 31 | 1.8 |
| 24 | tetrapropyl ammonium bromide | bistrifluoroacetylimide tetrapropylammonium salt | $^1$H-NMR: 0.92(t), 3.00(m), 3.63(m)<br>$^{19}$F-NMR: −76.65(s) | 83 | — |
| 25 | hexyltrimetyl ammonium bromide | bistrifluoroacetylimide hexyltrimetylammonium salt | $^1$H-NMR: 0.89(t), 1.31(m), 1.68(m), 3.05(s), 3.28(t)<br>$^{19}$F-NMR: −76.65(s) | −67 (Tg) | 1.8 |
| 26 | trimethyloctyl ammonium bromide | bistrifluoroacetylimide trimetyloctylammonium salt | $^1$H-NMR: 0.87(t), 1.28(m), 1.68(m), 3.05(s), 3.28(t)<br>$^{19}$F-NMR: −76.65(s) | −82 (Tg) | 1.1 |

TABLE 8

| example | raw material | product | NMR (ppm) | melting point (° C.) | ion conductivity (mS/cm) |
|---|---|---|---|---|---|
| 27 | 1-ethyl-3-metylimidazolium bromide | bistrifluoroacetylimide 1-ethyl-3-metylimidazolium salt | $^1$H-NMR: 1.43(t), 3.86(s), 4.20(q), 7.70(s), 7.79(s), 9.12(s)<br>$^{19}$F-NMR: −76.65(s) | 14 | 9.3 |
| 28 | tetraethyl phosphonium bromide | bistrifluoroacetylimide tetraetylphosphonium salt | $^1$H-NMR: 1.15(m), 2.23(m)<br>$^{19}$F-NMR: −76.65(s) | 22 | 6.7 |
| 29 | tetrabutyl phosphonium bromide | bistrifluoroacetylimide tetrabutylphosphonium salt | $^1$H-NMR: 0.92(t), 1.45(m), 2.19(m)<br>$^{19}$F-NMR: −76.65(s) | 64 | — |
| 30 | tetraoctyl phosphonium bromide | bistrifluoroacetylimide tetraoctylphosphonium salt | $^1$H-NMR: 0.87(t), 1.38(m), 2.17(m)<br>$^{19}$F-NMR: −76.65(s) | 4 | 0.5 |
| 31 | tetraphenyl phosphonium bromide | bistrifluoroacetylimide tetraphenylphosphonium salt | $^1$H-NMR: 7.76(m), 7.83(m), 7.98(m)<br>$^{19}$F-NMR: −76.65(s) | 115 | — |

Example 32

A sample solution was prepared by dissolving 0.33 g of lithium salt of bis trifluoromethanesulfon imide in 3.64 g of 2,2,2-trifluoro-N-(trifluoromethanesulfonyl) acetamide 1-ethyl-3-methylimidazolium salt produced in Example 10. A cyclic voltammetry measurement was carried out on the sample solution in the range of voltage of −3.6~0V of I$^-$/I$^{3-}$ electrode system by the use of "HSV-100AUTOMATIC POLARIZATION SYSTEM" (Trade Name) manufactured by HOKUTO DENKO CO. LTD. In the above-described cyclic voltammetry measurement, three types of electrodes were used; one is a nickel working electrode, the other is a platinum opposite electrode, and another is a reference electrode prepared by a method in which bis trifluoromethanesulfon imide 1-ethyl-3-methylimidazolium salt in which are dissolved 60 mmol/l of tetra-n-propylammonium iodide and 15 mmol/l of iodine is put in a glass tube partitioned by a porous Vycor glass, and then is dipped a platinum wire. Results of measurement are shown in FIG. 1. As shown in FIG. 1, oxidation-reduction of lithium was observed. The charge-discharge efficiency calculated by dividing the discharge capacity with the dissolution of lithium metal by the charge capacity was 60%.

Comparative Example 2

The cyclic voltammetry measurement was carried out by the use of the same procedures as those of Example 32 except that bis trifluoromethanesulfon imide 1-ethyl-3-methyl imidazolium salt was used instead of 2,2,2-trifluoro-N-(trifluoromethanesulfonyl)acetamide 1-ethyl-3-methylimidazolium salt. Results thus obtained were shown by a broken line in FIG. 1. In this measurement, discharge peak by dissolution of lithium metal was not observed and the charge-discharge efficiency was 0%. As shown in FIG. 1, while a peak was observed in the side of reduction, a peak in the side of oxidation corresponding to the peak in the side of reduction was not observed when the voltage was allowed to rise. Accordingly, it is considered that the decomposition of the cation of the above-described imidazolium salt occurs.

Example 33

The cyclic voltammetry measurement was carried out using the same procedures as those of Example 32 except that a mixture of bis trifluoromethanesulfon imide 1-ethyl-3-methyl imidazolium salt with 2,2,2-trifluoro-N-(trifluoromethanesulfonyl) acetamide 1-ethyl-3-methylimidazolium salt with the weight ratio of the former to the later in 9 to 1 instead of 2,2,2-trifluoro-N-(trifluoromethanesulfonyl)acetamide 1-ethyl-3-methylimidazolium salt. A discharge peak by dissolution of lithium metal was observed and the charge-discharge efficiency at the time was 50%.

Example 34

The cyclic voltammetry measurement was carried out for a solution prepared by dissolving 0.33 g of 2,2,2-trifluoro-N-

(trifluoromethanesulfonyl)acetamide lithium salt in 3.64 g of bis trifluoromethanesulfon imide 1-ethyl-3-methyl imidazolium salt using the same procedures as those of Example 32. A discharge peak by dissolution of lithium metal was observed and the charge-discharge efficiency at the time was 60%.

Example 35

The cyclic voltammetry measurement was carried out for a solution prepared in Comparative Example 2 by the use of the nickel working electrode used in Example 32 the surface of which was not polished. A discharge peak by dissolution of lithium metal was observed and the charge-discharge efficiency at the time was 50%.

Examples 36~41

The same procedures as those of Example 32 were repeated except that onium salts shown in Table 9 were used instead of 2,2,2-trifluoro-N-(trifluoromethanesulfonyl)acetamide 1-ethyl-3-methyl imidazolium salt. Charge-discharge efficiency was shown in Table 9.

TABLE 9

| Example | Onium salt | Charge-discharge efficiency (%) |
|---|---|---|
| 36 | 2,2,2-trifluoro-N-(trifluoromethanesulfonyl) acetamide triethylmethyl ammonium salt | 67 |
| 37 | 2,2,2-trifluoro-N-(trifluoromethanesulfonyl) acetamide tetraethyl ammonium salt | 62 |
| 38 | 2,2,2-trifluoro-N-(trifluoromethanesulfonyl) acetamide trimethylisopropyl ammonium salt | 56 |
| 39 | 2,2,2-trifluoro-N-(trifluoromethanesulfonyl) acetamide hexyltrimethyl ammonium salt | 60 |
| 40 | 2,2,2-trifluoro-N-(trifluoromethanesulfonyl) acetamide tetraethyl phosphonium salt | 54 |
| 41 | bistrifluoroacetylimide hexyltrimethyl ammonium salt | 60 |

Effect of the Invention

According to the invention described in claim 1: Since charge-discharge with oxidation-reduction of lithium is made possible even if an onium salt in liquid state at ordinary temperature which could not have been used as an electrolyte for a lithium battery by optimization of the interface of metal lithium negative electrode, the applications of the onium salt for an electrolyte and electrode can be expanded; That is to say, the treating method of the present invention expands the application as an electrolyte of the onium salt of which the use has been restricted due to low resistance to reduction despite of its superior property of showing liquid state at ordinary temperature. Furthermore, the treating method of the present invention makes it possible to design an electrochemical device such as a lithium primary battery, lithium secondary battery and so forth having long-term reliability, durability and safety.

According to the invention described in claim 2, the excessive activity of the surface of the negative electrode can be optimized, self-discharge can be suppressed and shelf life can be prolonged.

By applying the negative electrode according to the invention described in claim 3 to an electrochemical device such as a lithium battery, dye-sensitizing type-solar cell, capacitor, electrochromic device and so forth, the excessive activity of the surface of the negative electrode can be optimized, self-discharge can be suppressed and shelf life can be prolonged.

According to the invention described in claim 4, there is provided a novel onium salt. The novel onium salt has an excellent property that it can exhibit a low melting point even if it is combined with a cation having high symmetry and has low melting point compared with an onium salt which has the same kind of cation and an anion different from that of the onium slat of the present invention. Further, the ion conductivity of the onium salt described in claim 4 is high. Therefore, according to the invention described in claim 4, there are provided many onium salts showing a liquid state at low temperature and a series of novel onium salt having different properties. As a result, the invention described in claim 4 can expand the wide of selection of the materials usable for a non-aqueous electrolyte without using an organic solvent in the field of an electrochemical device using an electrolyte.

According to the invention described in claim 5, a novel and stable onium salt of the present invention can be obtained by selecting a proper ammonium cation or phosphonium cation or sulfonium cation.

According to the invention described in claim 6, there is provided a novel onium salt. The novel onium salt has an excellent property that it can exhibit a low melting point even if it is combined with a cation having high symmetry. Therefore, there are provided many onium salts showing a liquid state at low temperature and a series of novel onium salt having different properties. As a result, the invention described in claim 6 can expand the wide of selection of the materials usable for a non-aqueous electrolyte without using an organic solvent in the field of an electrochemical device using an electrolyte. According to the invention described in claim 6, a novel and stable onium salt of the present invention can be obtained.

According to the invention described in claim 7, there is provided an electrolyte which shows a high ion-conductivity in a wide range of temperature and has sufficient resistance to oxidation-reduction. That is to say, according to the invention described in claim 7, there is provided an excellent electrolyte which has a wide electric potential window and has high thermal stability in a wide range of temperature and low toxicity.

According to the invention described in claim 8, there is provided an excellent electrolyte which shows a high ion-conductivity in a wide range of temperature and has sufficient resistance to oxidation-reduction, that is to say, which has a wide electric potential window and has high thermal stability in a wide range of temperature and low toxicity and which is usable for an electrochemical device such as a lithium battery, dye-sensitizing type-solar cell, capacitor, electrochromic device and so forth.

According to the invention described in claim 9, there is provided an electrochemical device such as a lithium battery, dye-sensitizing type-solar cell, capacitor, electrochromic device and so forth which has the high electromotive force, and which is small and lightweight, and which has high energy density, and which is usable in a wide range of temperature, and which has little self-discharge, and which can be stored in for long periods.

Figure 1:
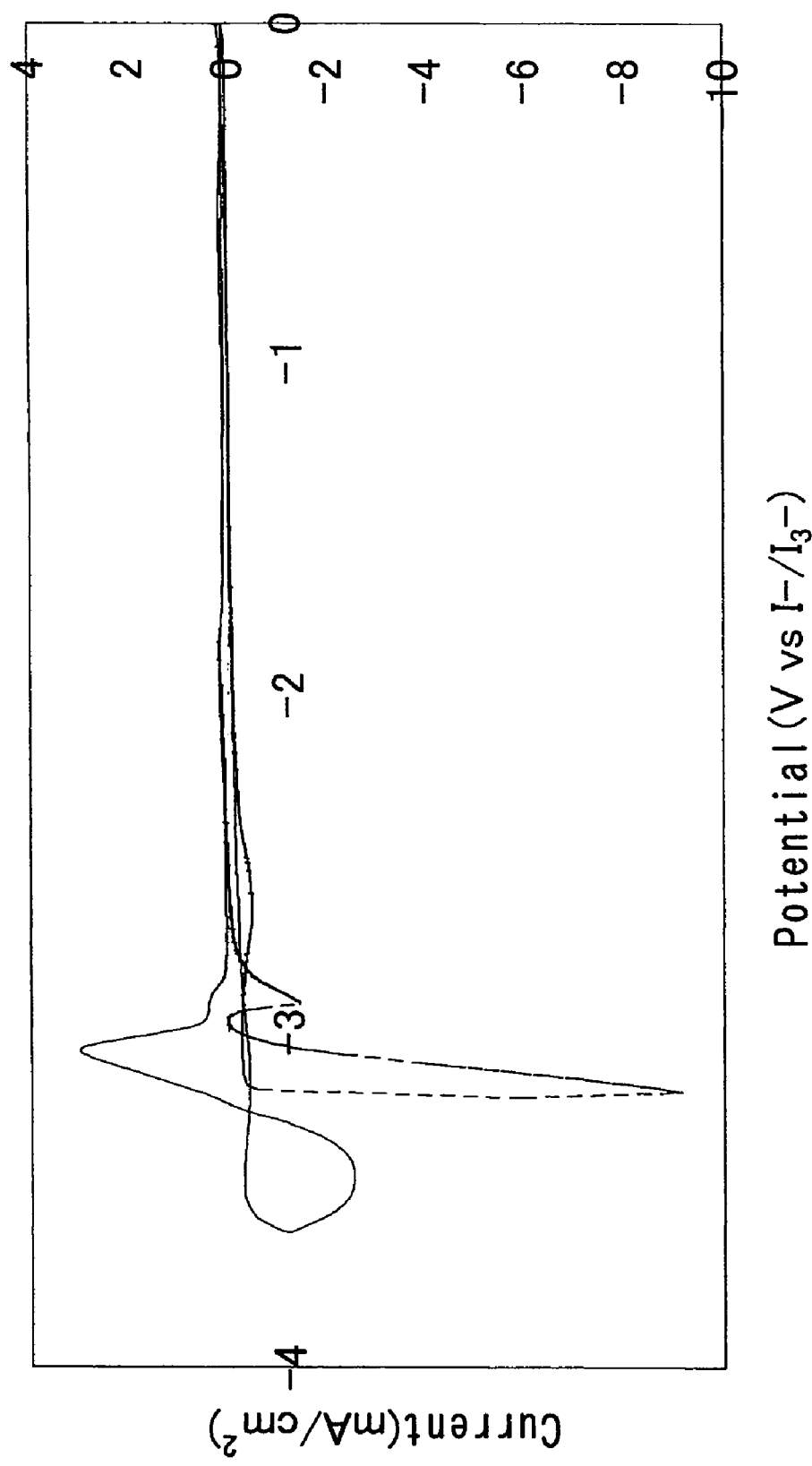
FIG. 1 shows cyclic voltanograms obtained in Example 32 and comparative Example 2.

The invention claimed is:

1. An onium salt illustrated by the general formula (V);

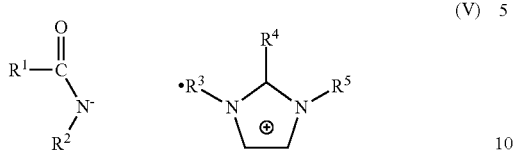

wherein $R^1$ is selected from the group consisting of a perfluoroalkyl group having 1 to 6 carbon atoms, a perfluoroalkyl group and a perfluoroaralkyl group having 7 to 9 carbon atoms, $R^2$ is selected from the group consisting of a formyl group, a acetyl group, a propionyl group, a butyryl group, a isobutyryl group, a valeryl group, a isovaleryl group, a pivaloyl group, a lauroyl group, a trifluoroacetyl group, a 2,2-difuluoropropionyl group, a perfuluoropropionyl group, a perfluorobutyryl group, a perfluoroisobutyryl group, a perfuluorovaleryl group, a methoxycarbonyl group, a ethoxycarbonyl group, a tert-butoxycarbonyl group, a trifuluoromethoxycabonyl group, a perfluoroethylcarbonyl group, a perfluoro-tert-butoxycarbonyl group, a methanesulfonyl group, a ethanesulfonyl group, a propanesulfonyl group, a tert-butanesulfonyl group, a trifluoromethanesulfonyl group, a pentafluoroethanesulfonyl group, a heptafluoropropanesulfonyl group, a nonafluorobutanesulfonyl group, a heptafluoroisopropanesulfonyl group, a nonafluoroisobutanesulfonyl group, a 2,2,2-trifluoroethanesulfonyl group, a 1,1-difuluoroethanesulfonyl group, a pentafuluorobenzenesulfonyl and a 2,4,6-trifuluorobenzenesulfonyl group, $R^4$ is a hydrogen atom, and $R^3$ and $R^5$ are, independently, selected from the group consisting of a methyl group, a ethyl group, a propyl group, a isopropyl group and a tert-butyl group.

2. An electrolyte comprising the onium salt of claim 1.

3. An electrolyte for a non-aqueous type-electrochemical device comprising the electrolyte of claim 2.

4. An electrochemical device comprising the electrolyte of claim 3.

* * * * *